(12) United States Patent
Jensen

(10) Patent No.: US 9,526,708 B2
(45) Date of Patent: Dec. 27, 2016

(54) METHODS FOR PROSTATECTOMY

(76) Inventor: James C. Jensen, Huntington, WV (US)

(*) Notice: Subject to any disclaimer, the term of this patent is extended or adjusted under 35 U.S.C. 154(b) by 882 days.

(21) Appl. No.: 13/540,418

(22) Filed: Jul. 2, 2012

(65) Prior Publication Data

US 2014/0323952 A1  Oct. 30, 2014

Related U.S. Application Data

(60) Provisional application No. 61/504,099, filed on Jul. 1, 2011.

(51) Int. Cl.
*A61K 31/137* (2006.01)
*A61B 17/00* (2006.01)

(52) U.S. Cl.
CPC ............ *A61K 31/137* (2013.01); *A61B 34/30* (2016.02); *A61B 17/00234* (2013.01); *A61B 2017/00274* (2013.01); *A61M 2210/166* (2013.01)

(58) Field of Classification Search
CPC .............. A61B 2017/00274; A61B 17/00234; A61M 2210/166; A61M 2210/167
See application file for complete search history.

(56) References Cited

U.S. PATENT DOCUMENTS

| | | | | |
|---|---|---|---|---|
| 2003/0055114 A1* | 3/2003 | Young | ............... | A61K 31/045 514/729 |
| 2006/0276871 A1* | 12/2006 | Lamson | ............... | A61F 2/82 623/1.11 |
| 2010/0312054 A1* | 12/2010 | Beyar | ............... | A61B 1/00082 600/108 |

OTHER PUBLICATIONS

Montague, Drogo K., Jonathan Jarow, Gregory Broderick, Jeremy Heaton, Tom Lue, Ajay Nehra, and Ira Sharlip. "Guideline on the Management of Priapism." American Urological Association: 15-16. Web. Mar. 3, 2016.*
Stirling, Brian N., et al. "Comparison of local anesthesia techniques during transrectal ultrasound-guided biopsies." Urology 60.1 (2002): 89-92.*
Lacks, Cecilia. "Dr. Catalona Discusses Nerve-Sparing Surgery." Dr. Catalona Discusses Nerve-Sparing Surgery. Web. Mar. 3, 2016.*

* cited by examiner

*Primary Examiner* — Imani Hayman
*Assistant Examiner* — Nilay Shah
(74) *Attorney, Agent, or Firm* — Thorpe North & Western LLP

(57) ABSTRACT

A method of reducing nerve damage associated with prostatectomy in a human subject includes the steps of infiltrating a phenylephrine containing solution into the prostate and/or regions adjacent to the prostate and performing a prostatectomy on the human subject. The methods reduce nerve damage often caused by prostatectomy and thereby increase a subject's odds for recovery of full sexual potency as well as complete continence.

12 Claims, 4 Drawing Sheets

METHODS FOR PROSTATECTOMY

PRIORITY

This application claims the benefit of U.S. Provisional Patent Application No. 61/504,099, filed on Jul. 1, 2011, and which is herein incorporated by reference.

BACKGROUND

A major goal of modern radical prostatectomy is the preservation of the unmyelinated autonomic fibers serving the corpus cavernosum, because injury to these fibers is associated with post-operative erectile dysfunction. Thermal injury is well known to cause problems with erectile dysfunction, as is mechanical injury due to excision, traction, or blunt injury. As such, the avoidance of electrocautery as a source of thermal injury during surgery is one method of achieving the objectives of Anatomical prostatectomy.

Several methods of non-cautery prostatectomy have been proposed including the extensive use of ligatures, surgical clips, vascular bulldogs, bioadhesives and sealants, and the employment of bipolar as opposed to monopolar cautery for hemostasis. However, such methods seem directed at controlling the major vascular structures such as the Dorsal Venous Complex and Lateral Vascular Pedicles of the prostate while significant intra operative and post-operative bleeding may occur due to bleeding at the arteriolar and capillary level such as on the bladder neck and periprostatic tissues, and pre rectal plane containing and including the neurovascular bundles. It has observed by many that surgeons generally fall back upon cautery when bleeding occurs at these sites (William Catalona, *American Urological Association Meeting Prostate Cancer Review Course, San Francisco*, 2010). Therefore, no method of non-cautery prostatectomy has gained wide acceptance or emerged giving reliable results in terms of sexual or urinary function.

Accordingly, research continues in an effort to discover methodologies for performing a radical prostatectomy that is nerve sparing without the need for electro-cautery, in general, and monopolar electro-cautery, in particular.

SUMMARY OF THE INVENTION

The present invention provides for methods of reducing nerve damage associated with prostatectomy. In one embodiment, a method of reducing nerve damage associated with prostatectomy in a human subject includes the steps of infiltrating a phenylephrine containing solution into the prostate and/or regions adjacent to the prostate and performing a prostatectomy on the human subject. The methods reduce nerve damage often caused by prostatectomy and thereby increase a subject's odds for recovery of full sexual potency as well as complete continence.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
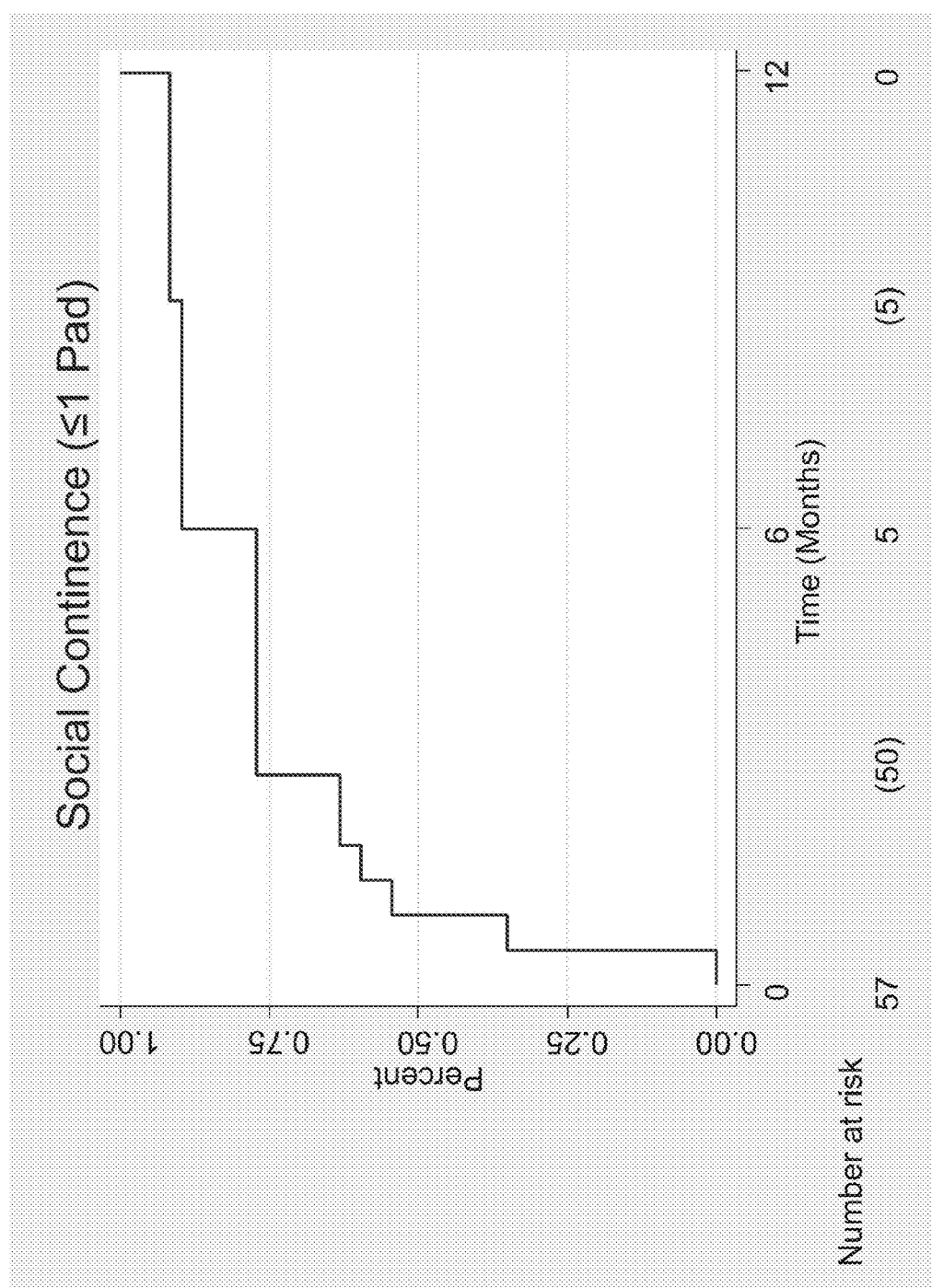
FIG. 1 shows a Kaplan Meier plot of the number of subjects and their social continence numbers following surgery.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present methods for the delivery and use of phenylephrine are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, "subject" refers to a human male subject.

As used herein, the term "prostatectomy" or "surgical prostatectomy" are used interchangeably and refer to the surgical removal of all or part of the prostate gland. The prostatectomy can be performed by any surgical technique known in the art such as including transurethral resection of the prostate (TURP), conventional (monopolar) TURP, bipolar TURP, laser prostate surgery, open prostatectomy techniques such as radical retropubic prostatectomy, radical perineal prostatectomy, suprapubic transvesical prostatectomy, laparoscopic radical prostatectomy, and computer-assisted laparoscopic radical prostatectomy (CALP) or robotic radical prostatectomies.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

Nerve Damage caused by prostatectomy can result in undesirable side effects including partial or complete loss of continence and/or partial or complete loss of potency. Accordingly, the present invention provides for methods of reducing nerve damage associated with prostatectomy. In one embodiment, a method of reducing nerve damage associated with prostatectomy in a human subject includes the steps of infiltrating a phenylephrine containing solution into the prostate and/or regions adjacent to the prostate and performing a prostatectomy on the human subject. In one aspect, the reduction in nerve damage using the method of the present invention is measured as compared to a prostatectomy using a similar technique. Thus, for example, if the method of the present invention is performed using Robotic Radical Prostatectomy, the nerve reduction of the method should be compared with prostatectomy using the same surgical technique without the infiltration of phenylephrine. Another benefit of the methods of the present invention is the ability of the prostatectomy to be accomplished without the need for cauterization.

The prostatectomy technique used in the methods of the present invention can generally be any known prostatectomy technique known in the art so long as the technique can be used in conjunction with the infiltration of phenylephrine as required by the disclosed method. Non-limiting examples of prostatectomy techniques that can be used in the methods of the present invention include transurethral resection of the prostate (TURP), conventional (monopolar) TURP, bipolar TURP, laser prostate surgery, open prostatectomy techniques such as radical retropubic prostatectomy, radical perineal prostatectomy, suprapubic transvesical prostatectomy, laparoscopic radical prostatectomy, computer-assisted laparoscopic radical prostatectomy (CALP), and robotic radical prostatectomies. Other techniques may also be useful for use in the disclosed methods.

When discussing infiltration of the phenylephrine containing solutions in the prostate and/or regions adjacent to the prostate can refer to the injection of the phenylephrine containing solution into these physiological regions. In one embodiment, the phenylephrine solution can be infiltrated into the prostate. In another embodiment, the phenylephrine containing solution can be infiltrated into regions adjacent to the prostate. Regions adjacent to the prostate that can be infiltrated with the phenylephrine solution can include vascular pedicles such as the left and right prostatic vascular pedicles, the anterior bladder neck, the lateral bladder neck, the left and right posterior bladder neck, the neurovascular margin and combinations thereof. The infiltration of the phenylephrine containing solution can occur prior to the prostatectomy, during the prostatectomy, or both.

The phenylephrine solutions used in the methods of the present invention can be pre-prepared or prepared immediately before use. The phenylephrine solutions can include the phenylephrine and a physiologically and pharmacologically acceptable carrier liquid. The carrier liquid can be water or an aqueous based carrier with other components such as salts or other drugs. In one embodiment, the carrier liquid is water. The phenylephrine containing solutions used in the methods of the present invention can have concentrations of 50 mcg/mL to about 200 mcg/mL. In another embodiment, phenylephrine containing solution can have a phenylephrine concentration of about 80 mcg/mL to about 120 mcg/mL.

In one embodiment, the present invention can provide for a sterile surgical kit for use in prostatectomy. Specifically, the kit can include pre-prepared phenylephrine solutions having concentrations of phenylephrine of 50 mcg/mL to about 200 mcg/mL for use during the performance of the prostatectomy. The kit can further include other surgical materials known in the art including one or more syringes, one or more needles for use with a syringe to inject the phenylephrine solution, etc.

The phenylephrine solutions are infiltrated into the prostate and/or regions adjacent to the prostate immediately prior to or during the prostatectomy. The total amount of phenylephrine infiltrated into the prostate and regions proximate the prostate can vary depending on the precise nature of the surgery (e.g. complete removal of the prostate vs. partial removal) as well as the individual subject. In one embodiment, the total of amount of phenylephrine infiltrated into the prostate or regions adjacent to the prostate can be from about 1000 micrograms to about 7000 micrograms. In another embodiment, the a total of amount of phenylephrine infiltrated into the prostate or regions adjacent to the prostate can be from about 2000 micrograms to about 6000 micrograms. In another embodiment, the total amount of phenylephrine infiltrated into the prostate or regions adjacent to the prostate can be from about 3000 micrograms to about 5500 micrograms.

EXAMPLES

The following examples are provided to promote a more clear understanding of certain embodiments of the present invention, and are in no way meant as a limitation thereon.

Example

Phenylephrine for Hemostasis During Robotic Radical Prostatectomy

A group of men who were in need of a prostatectomy were tested. All men undergoing robotic radical prostatectomy after June 2009 were given informed consent regard to and asked to participate in a prospective study of outcomes of robotic radical prostatectomy. Baseline data were obtained preoperatively with regard to sexual and urinary function using self-administered International Index of Erectile Function and International Prostate Symptom Score Questionnaires. Additionally, patients were asked if they had experienced intercourse, urinary incontinence or pad used in the 4 weeks prior to the initial screening visit. Only patients with a pre-operative score on the International Index of Erectile Function of greater than or equal to 20 were included in the post-operative analysis of continence and potency.

A standard method of prostatectomy was used except that hemostasis was achieved by the infiltration of phenylephrine at a concentration of 100 micrograms per milliliter into the anterior and antero lateral bladder neck (1000 micrograms), right lateral bladder neck (1,000 micrograms), left lateral bladder neck (1,000 micrograms), right prostatic vascular pedicle and neurovascular margin (1,000 micrograms) and left prostatic vascular pedicles and neurovascular margin (1,000 micrograms) for a total of 5,000 micrograms of the agent. Sharp cold dissection was then performed with either the Snap Blade or the Shears with rare spot use of bipolar cautery. Monopolar cautery was not used during any part of the procedure.

The Anesthesia Estimated blood loss was measured and represented the aggregate of blood loss, minus measured irrigation and estimated urine output. Patient hemoglobin and hematocrit were assessed pre-operatively, immediately post-operatively, and on post-operative day 1. Additionally, blood transfusion was recorded, and validated by examining blood bank records postoperatively. No blood transfusions were administered in the absence of indications such as hemoglobin less than 8.0 mg percent and or symptoms associated with acute surgical anemia (tachypena, chest pain, cardiac arrhythmia, etc.).

Continence was assessed in the post-operative period by pad use with one pad per day or less being considered as "socially continent." The use of zero pads per day was considered "absolutely continent" Or "complete continence." The time necessary to achieve each of these milestones was recorded individually for each subject. The end point of sexual recovery was intercourse, and the experience of intercourse was monitored at each post-operative visit. Intercourse was experienced by 21% of men within the 4 weeks prior to initial evaluation. It is noteworthy that two (2) weeks lapsed between the surgery and the removal of the urinary catheter, thus the initial evaluation of sexual function occurred 2 weeks following removal of the catheter, or 4 weeks following surgery. Additional follow-up evaluations were done at 8 and 12 weeks post-operative time points. Thereafter, men were seen at 6 and 12 months post operative time points. Intercourse at the 9 month interval (39 weeks) was established by phone interview in those men not reporting intercourse at the 6 month visit, and for whom interim follow up was not scheduled.

All patients in this study were given informed consent for participation in a prospective study of outcomes of robotic radical prostatectomy. No patients withdrew. Fifty seven (57) men among all patients operated had IIEF scores of 20 or greater. Two patients refused or were lost to follow-up for other reasons. All observations were collected in a prospective fashion and maintained in our IRB approved database of patients having robotic surgery.

Analysis of differences in means was performed by Student's t-test. The differences in proportions were calculated by the Chi-squared test. The probability of return of social continence, absolute continence, and the probability of intercourse was calculated by the Kaplan Meier function. Table I shows the statistical outcomes for the test subjects at various pre- and post-surgical time periods.

TABLE I

| Postoperative Time Weeks | Number of Patients | Social Continence Number (%) | Complete Continence Number (%) | Potency Number (%) |
| --- | --- | --- | --- | --- |
| 0 | 57 | 57 (100%) | 57 (100%) | 51 (89%) |
| 2 | 57 | 20 (35%) | 10 (18%) | 7 (12%) |
| 4 | 57 | 31 (54%) | 17 (30%) | 12 (21%) |

TABLE I-continued

| Postoperative Time Weeks | Number of Patients | Social Continence Number (%) | Complete Continence Number (%) | Potency Number (%) |
| --- | --- | --- | --- | --- |
| 6 | 57 | 32 (56%) | 16 (28%) | 14 (25%) |
| 8 | 56 | 33 (58%) | 17 (30%) | 15 (27%) |
| 12 | 55 | 40 (73%) | 20 (36%) | 23 (42%) |
| 26 | 46 | 40 (87%) | 26 (57%) | 24 (52%) |
| 39 | 38 | 34 (89%) | 24 (63%) | 20 (53%) |
| 52 | 37 | 37 (100%) | 35 (95%) | 34 (92%) |
| 78 | 23 | 23 (100%) | 23 (100%) | 23 (100%) |

Figure 2:
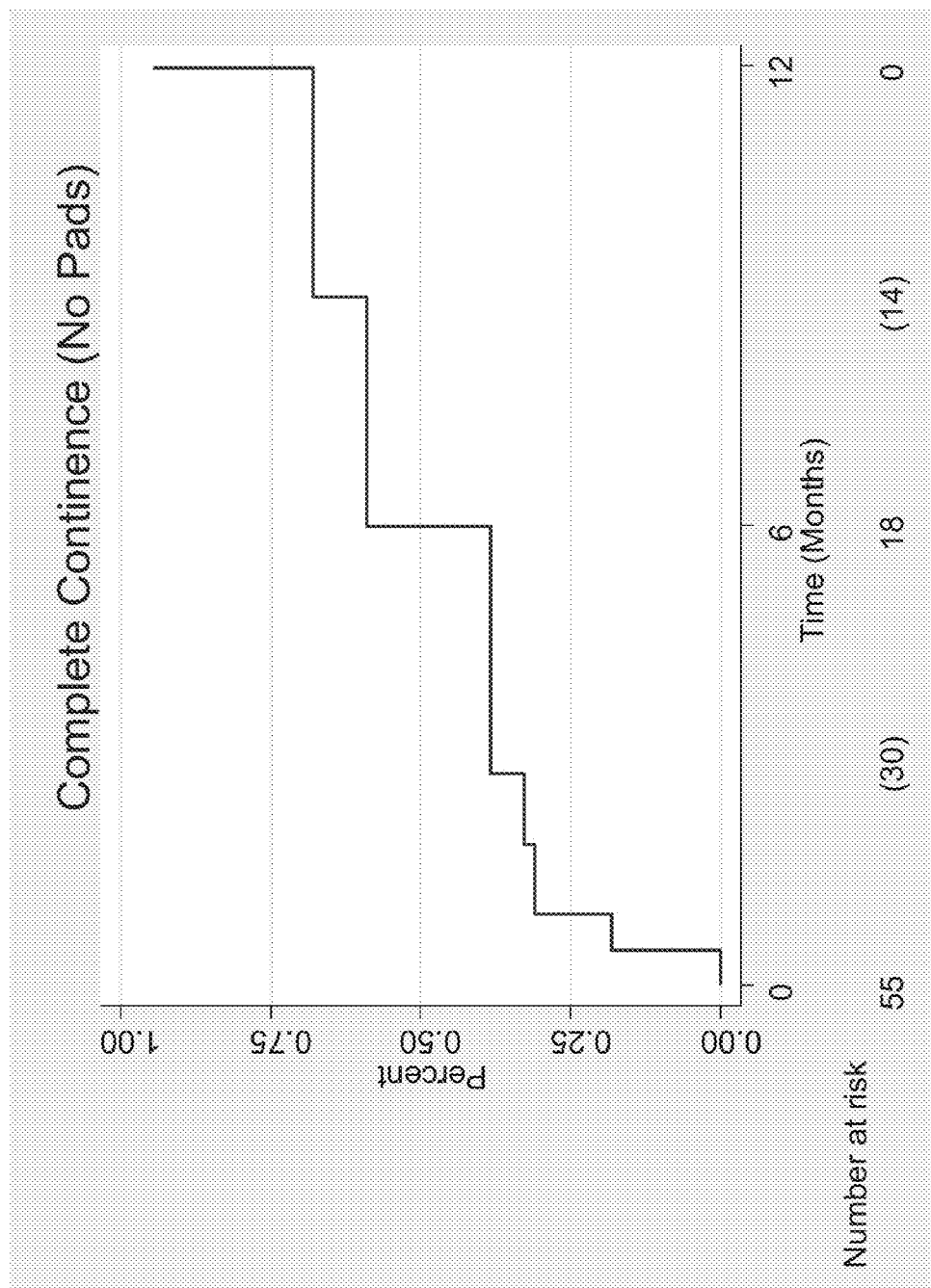
FIG. 2 is a Kaplan Meier plot of the number of subjects and their complete continence following surgery.
Figure 3:
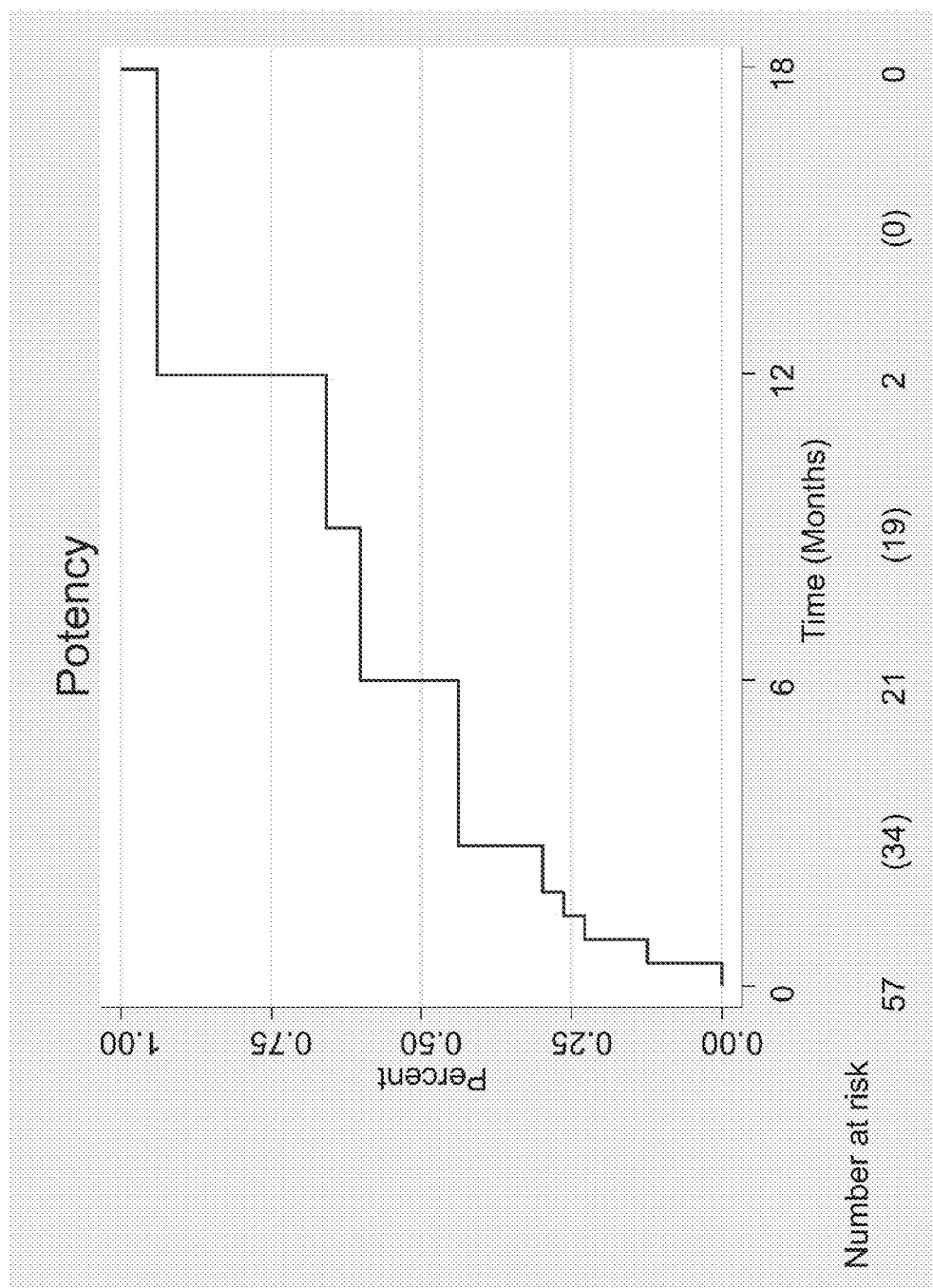
FIG. 3 shows a Kaplan Meier plot of subjects and their potency following surgery.

FIG. 1 shows a Kaplan Meier plot of the number of subjects and their social continence numbers following surgery. It is notable that 100% of the subjects at risk at the 52-week mark had social continence. FIG. 2 is a Kaplan Meier plot of the number of subjects and their complete continence following surgery. Complete continence was achieved for 100% of the subjects at the 78-week time point. FIG. 3 shows a Kaplan Meier plot of subjects and their potency following surgery. Complete potency was achieved at the 78-week time point.

An ongoing study of the 57 subjects described above as well as an additional 23 new subjects was also performed. Table II shows the statistical outcomes for the test subjects at various pre- and post-surgical time periods.

TABLE II

| Weeks Post Op | Number of Patients | Intercourse* | One or less pad per 24 hours | Zero Pads per 24 hours |
| --- | --- | --- | --- | --- |
| 0 (Pre Op) | 80 | 90% | 100% | 99% |
| 2 | 79 | 10% | 32% | 18% |
| 4 | 78 | 19% | 49% | 28% |
| 6 | 77 | 25% | 58% | 27% |
| 8 | 77 | 27% | 60% | 28% |
| 12 (3 mos) | 77 | 42% | 73% | 36% |
| 26 (6 mos) | 71 | 58% | 89% | 52% |
| 39 (9 mos) | 63 | 67% | 92% | 65% |
| 52 (12 mos) | 53 | 83% | 100% | 85% |
| 78 (1.5 yrs) | 30 | 77% | 100% | 83% |
| 104 (2.0 yrs) | 14 | 93% | 100% | 93% |

*Sexual function (intercourse) reflects the use of phosphodiesterase inhibitors such as Cialis ™, Viagra ™, and Levitra ™.

Figure 4:
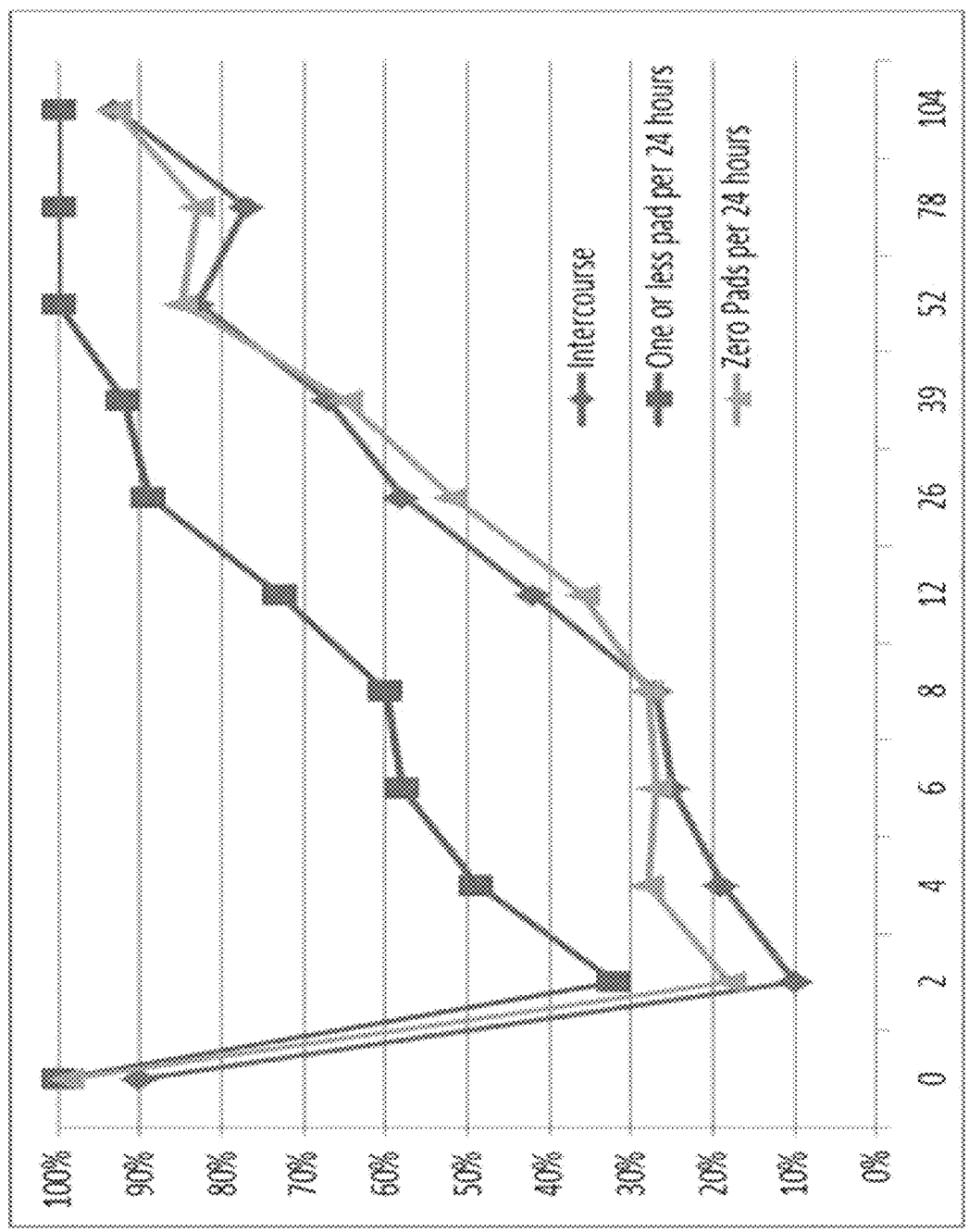
FIG. 4 shows a plot of the percentage of subjects experiencing a number of parameters (including intercourse, one or less pads per week, and zero pads per week) over the weeks following the prostatectomy.

FIG. 4 shows a plot of the percentage of subjects experiencing a number of parameters over the weeks following the prostatectomy. As can be seen in FIG. 4, social continence for all subjects was achieved within about 52 weeks following surgery, with absolute continence being achieved in more than 80% of subjects over the same time period. Sexual function (intercourse) for also achieved for about 80% of subjects within about 52 weeks following surgery.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method comprising:
   reducing nerve damage associated with prostatectomy in a human subject by infiltrating a phenylephrine containing solution into a prostate of the subject or regions adjacent to the prostate, and performing a prostatectomy on the subject.

2. The method of claim 1, wherein a total amount of phenylephrine infiltrated into the prostate is from about 1000 micrograms to about 6000 micrograms.

3. The method of claim 1, wherein a total amount of phenylephrine infiltrated into the prostate is from about 4000 micrograms to about 5500 micrograms.

4. The method of claim 1, wherein the phenylephrine containing solutions are infiltrated into the regions adjacent to the prostate.

5. The method of claim 1, wherein the infiltrating is done immediately prior to the prostatectomy.

6. The method of claim 1, wherein the infiltrating is done during the prostatectomy.

7. The method of claim 1, wherein no cauterization is used during the prostatectomy.

8. The method of claim 1, wherein the prostatectomy is accomplished using a technique selected from the group consisting of Transurethral resection of the prostate (TURP), Conventional (monopolar) TURP, Bipolar TURP, Laser prostate surgery, Radical retropubic prostatectomy, Radical perineal prostatectomy, Suprapubic transvesical prostatectomy, Laparoscopic radical prostatectomy, Computer-assisted laparoscopic radical prostatectomy (CALP), and Robotic radical prostatectomies.

9. The method of claim 1, further comprising infiltrating the phenylephrine containing solution into the prostate of the subject and regions adjacent to the prostate.

10. The method of claim 9, wherein the phenylephrine containing solution has a phenylephrine concentration of about 50 mcg/mL to about 200 mcg/mL.

11. The method of claim 9, wherein the phenylephrine containing solution has a phenylephrine concentration of about 80 mcg/mL to about 120 mcg/mL.

12. The method of claim 9, wherein the phenylephrine containing solutions are infiltrated into a region adjacent to the prostate selected from the group consisting of vascular pedicles, anterior bladder neck, lateral bladder neck, posterior bladder neck, and combinations thereof.

* * * * *